United States Patent [19]
Davidson

[11] 3,948,255
[45] Apr. 6, 1976

[54] APPARATUS FOR ENDOTRACHEAL AND ESOPHAGEAL INTUBATION

[76] Inventor: Kenneth L. Davidson, 12735 11th Ave., Victorville, Calif. 92392

[22] Filed: Jan. 20, 1975

[21] Appl. No.: 542,212

Related U.S. Application Data

[62] Division of Ser. No. 476,955, June 6, 1974, Pat. No. 3,874,377.

[52] U.S. Cl. ............. 128/145.5; 128/274; 128/211; 128/210; 137/625.46
[51] Int. Cl.² .................................... A61M 16/00
[58] Field of Search......... 128/145.5, 145 R, 145 A, 128/145.6, 145.7, 145.8, 146.4, 147, 203, 205, 207, 208, 209, 210, 211, 277, 274; 137/625.46

[56] References Cited
UNITED STATES PATENTS

| 733,026 | 7/1903 | Goldan | 128/209 |
|---|---|---|---|
| 3,683,908 | 8/1972 | Don Michael et al. | 128/351 |
| 3,814,092 | 6/1974 | Simionescu et al. | 128/145.5 |

*Primary Examiner*—Robert W. Michell
*Assistant Examiner*—Henry J. Recla
*Attorney, Agent, or Firm*—Fulwider Patton Rieber Lee & Utecht

[57] ABSTRACT

Apparatus for use in artificial respiration and the like, comprising an elongated tubular body having a flexible inner end portion adapted for insertion in the esophagus or trachea of a patient and an outer end portion for connection to a source of fluid. An inflatable cuff is carried at the inner end portion. The upper end portion of the tubular body includes an adapter, a seal for the lumen of the tubular body carried by the adapter and a plurality of closable openings spaced in the upper portion between the seal and the outer end of the tubular body. In the esophageal mode, the lumen of the tubular body is sealed to prevent the flow of fluids between the upper portion and lower portion of the tubular body. The openings in the upper portion are open to permit the flow of fluid therethrough into the patient's trachea and lungs. In the tracheal mode, the openings in the upper portion are closed, and the lumen of the tubular body is open to provide fluid communication through the tubular body.

4 Claims, 7 Drawing Figures

U.S. Patent  April 6, 1976  3,948,255
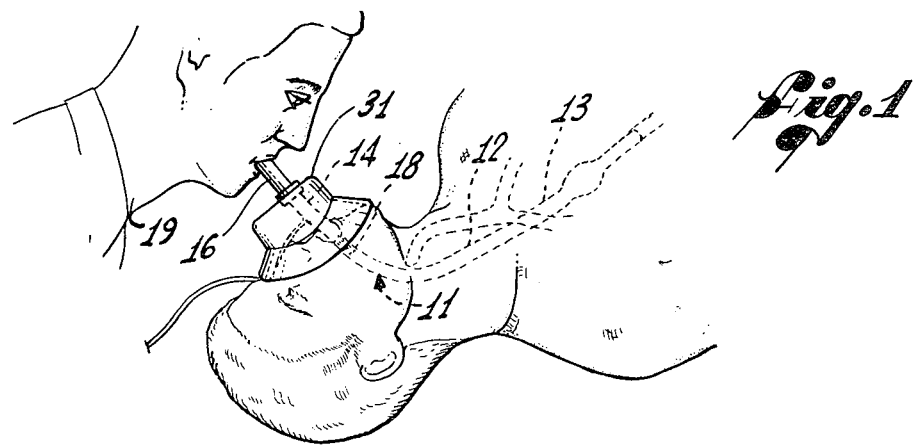
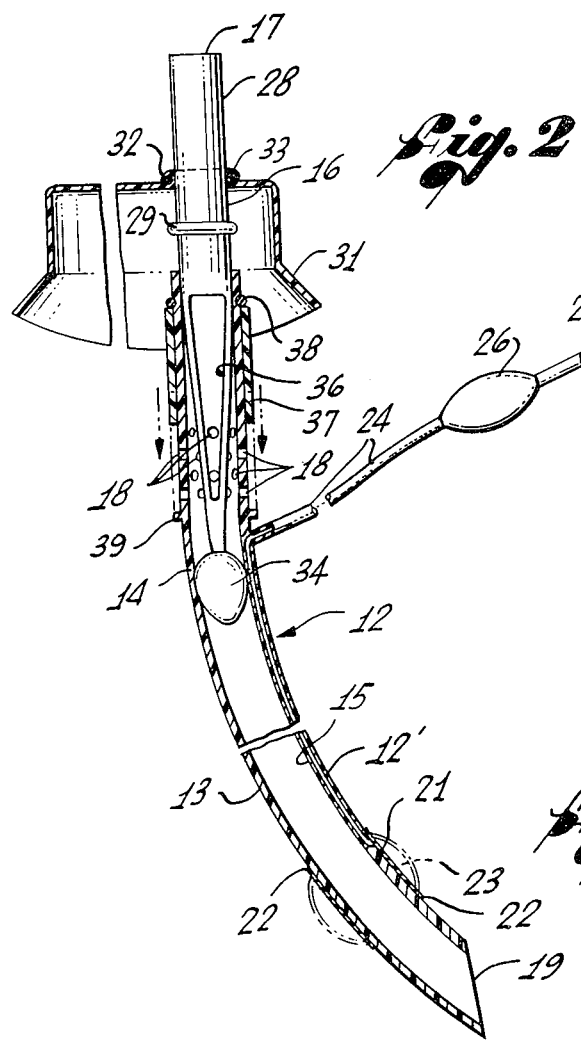
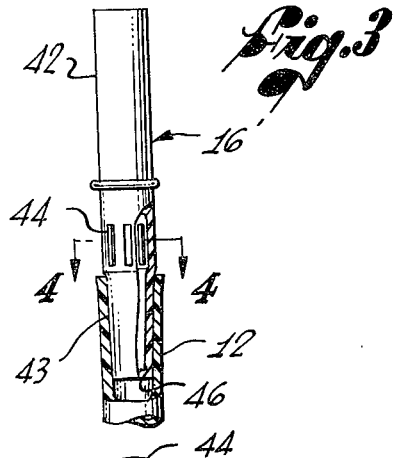
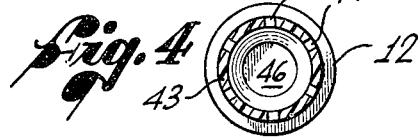
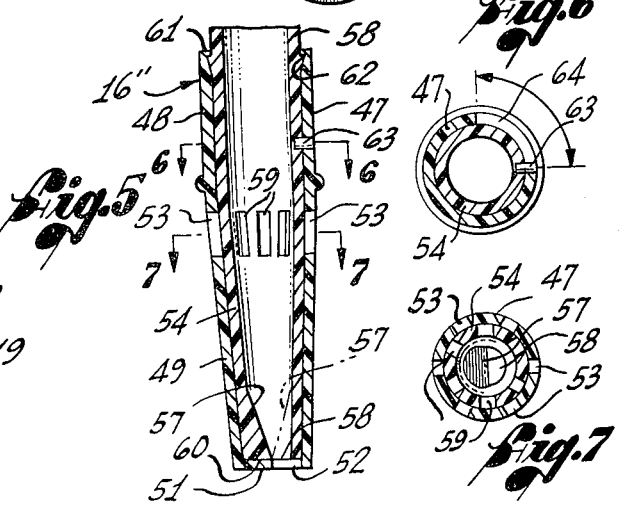

APPARATUS FOR ENDOTRACHEAL AND ESOPHAGEAL INTUBATION

This is a division, of application Ser. No. 476,955, filed June 6, 1974 now U.S. Pat. No. 3,874,377.

BACKGROUND OF THE INVENTION

This invention relates to apparatus for the introduction of fluids such as air, oxygen, anesthetics and the like into a patient's lungs and more particularly to a tubular body adapted for both endotracheal and esophageal intubation.

It is often necessary or desirable in surgical procedures and the like to control the patient's breathing by intubation of the patient's trachea for the introduction of air, oxygen or anesthetic into the patient's respiratory system. Intubation devices ordinarily include an elongated flexible tubular body and an inflatable cuff is normally provided on a portion of the tube which is inserted in the patient's trachea to provide a seal between the tracheal lining and the walls of the tube. The end of the tube opposite the inserted end is adapted for connection to suitable apparatus for the introduction of air, oxygen, anesthetic or the like. Examples of such devices are disclosed in U.S. Pat. Nos. 3,460,541, Doherty and U.S. Pat. No. 3,599,642, Tindel. Such endotracheal devices, although successful in maintaining an open airway for the patient can be difficult to insert, particularly in case of an emergency, and normally require the services of a highly skilled person for proper insertion of the device without injuring the patient.

A second type of intubation device has been used, particularly in emergency situations where prompt administration of artificial respiration is critical. Such devices are elongated tubular bodies which are designed to be inserted into the patient's esophagus and which are provided with a plurality of openings spaced on the upper portion of the tubular body for fluid communication with the patient's respiratory passage. The use of such a device ordinarily results in the inflation of the patient's stomach which can result in the flow of stomach contents back up through the tube. Such counterflow of stomach contents is both unpleasant to a person administering artificial respiration and is also dangerous to the patient since some of the stomach fluids may enter the respiratory passages and eventually the lungs of the patient. To avoid this, apparatus designed for esophageal intubulation can be sealed at the inner end to prevent inflation of the stomach with air, oxygen or the like and to prevent the counterflow of stomach fluids up through the tube. An example of such a device is disclosed in U.S. Pat. No. 3,683,908 Don Michael, et al.

Generally speaking, and circumstances permitting, endotracheal intubation is preferred over esophageal intubation as being the most efficient method for introduction of fluids into the patient's lungs. However, where time does not permit, or where skilled personnel are not available, esophageal intubation is utilized since it is quicker and easier to insert a tube into the patient's esophagus without risk of serious injury to the patient.

From the above discussion it can be seen that it is necessary for a hospital and/or emergency facilities such as fire departments and the like, to stock both endotracheal and esophageal intubation tubes in order to be prepared for the eventuality that one or the other procedure will be required for the proper treatment of the patient. This unduly multiplies the number and type of intubation devices required to be on hand and adds to the expense of hospital and emergency facility operations. Also, in connection with esophageal intubation, in approximately 20% of esophageal insertions the tube will accidently enter the trachea resulting in a blockage of the patient's airway, if a conventionally sealed tube is being used.

SUMMARY OF THE INVENTION

The present invention resides in apparatus which is readily adapted for use both in endotracheal and esophageal intubation procedures. In accordance with the present invention, the apparatus is quickly and easily modified to operate either as an esophageal intubation device or endotracheal intubation device depending on whichever procedure is indicated under the circumstances.

More particularly, the apparatus of the present invention comprises an elongated tubular body having open ends and a throughrunning lumen. The tubular body further defines a flexible, lower end portion for insertion in the patient's esophagus or trachea and an upper end portion which includes an adapter for connection of the tubular body to a source of fluid.

An inflatable cuff is positioned about the tubular body at the lower portion thereof. As is standard practice, the cuff is inflated after insertion of the lower portion of the tubular body in the patient's esophagus or trachea to provide a seal with the walls of the esophagus or trachea.

The adapter is partially inserted in the flexible tube and the inserted end thereof is modified for selectively sealing the lumen of the tubular body when the apparatus is in the esophageal intubation mode and the opposite, extending end of the adapter defines the outer end of the tubular body for connection to a source of fluid. At least one open discharge port is located at the outer end portion of the tubular body in spaced relation with the seal when the apparatus is in the esophageal mode.

In the endotracheal mode the seal is removed from the lumen and the discharge port closed for direct fluid communication between the ends of the tubular body. During the insertion procedure, particularly into the esophagus, the apparatus is in the endotracheal mode with the lumen unsealed to provide an unrestricted airway in order to avoid the risk of unintentionally blocking the patient's airway.

Other objects and advantages of the present invention will become apparent from the following detailed description and taken in conjunction with the accompanying drawings.

BRIEF DESCRIPTION OF THE DRAWINGS

FIG. 1 illustrates the apparatus of the present invention partially in solid line and partially in broken line inserted in the esophagus of a patient as employed in esophageal intubation;

FIG. 2 is an enlarged side view, partially in section and partially broken away for compactness of illustration, of the apparatus of the present invention in the esophageal intubation mode;

FIG. 3 is a side elevation, partially broken away and partially in section, showing another embodiment of an adapter for use in the apparatus of the present invention for adapting the apparatus for esophageal intubation;

FIG. 4 is an enlarged sectional view taken through line 4—4 of FIG. 3;

FIG. 5 is a side sectional view of another adapter used in the apparatus of the present invention;

FIG. 6 is a top sectional view taken through line 6—6 of FIG. 5; and

FIG. 7 is a top sectional view taken through line 7—7 of FIG. 5.

DETAILED DESCRIPTION OF THE INVENTION

As illustrated in the drawings, the invention is embodied in apparatus, indicated generally as 11, for endotracheal and esophageal intubation comprising a tube 12 having a throughrunning lumen 15 and defining a flexible inner portion 13 adapted for insertion in the trachea or esophagus of a patient and an outer portion 14 adapted for connection to a source of air, oxygen, anesthetic and the like. The outer portion 14 includes an adapter 16 which is inserted part way in the tube 12 and which extends beyond the end of the tube to define an open outer end 17 for connection to a source of fluid. The adapter 16 is modified for sealing the tube in the esophageal mode. At least one discharge opening 18 is located in the outer portion 14 of the tube 12 for fluid communication between the source of fluid and the respiratory tract of the patient when the apparatus is in the esophageal mode. When the lumen 15 of the tube 12 is open, the wall of the upper portion 14 is made continuous, such as by means carried on the upper portion of the tube for closing the opening 18 to provide fluid communication through the entire length of the lumen of the tube when the apparatus is in the endotracheal mode.

As illustrated in FIGS. 1 and 2, the apparatus of the present invention is shown in the esophageal mode with the inner portion 13 of the tube 12 inserted in the esophagus and with the outer end portion 14 extending through the mouth and lips of the patient to a source of air, in this case an operator 19 applying artificial respiration.

As is more specifically shown in FIG. 2, the tube 12 is open-ended and flexible with the lumen 15 unrestricted along the length of the tube. The adapter 16 is inserted part way in one end of the tube 12 so that a portion of the adapter is contained in the lumen 15. The part of the tube containing the adapter and the adapter itself comprise the outer portion 14 and the remaining part of the tube comprises the flexible inner portion 13 adapted to be inserted in the esophagus or the trachea of the patient. The end of the lower portion is biased, as at 19, as an aid in inserting the tube.

A resilient cuff 21 surrounds the tube 12 adjacent the end of the inner portion 13. The cuff is bonded to the tube 12 at its edges 22 to provide a chamber 23 between the inner surface of the cuff and the underlying outer surface of the tube. A duct 12 extends along a side wall of the tube 12 between the outer portion 14 and the inner portion 13 of the tube and communicates at one end with the chamber 23 and at its opposite end with a small air tube 24 and a bulb 26 provided with a removable plug 27 for holding the necessary pressure to maintain the cuff in an inflated condition and removable for inflating and deflating the cuff.

The adapter 16 is removably inserted in the tube 12 and includes a cylindrical extending portion 28, the open outer end of which defines the outer end 17 of the apparatus 11 for connection to a source of fluid. A gripping ring 29 is provided on the exterior surface of the cylindrical portion 28 as an aid for inserting and removing the adapter. A face mask 31 may be integrally formed on the cylindrical portion 28 of the adapter or may be removably clamped thereon, such as by a clamp 32 and screws 33.

The opposite end of the adapter carried within the tube is closed and defines an enlarged bulbous plug 34 which is sized so as to provide a fluid tight seal with the walls of the tube 12. Elongated slots 36, 38 are provided in the wall of the portion of the adapter 16 extending within the tube 12 for communication between the interior of the adapter 16 and the lumen 15 of the tube. The portion of the adapter 16 carried within the tube 12 is preferably curved so, in combination with the tube, the outer portion 14 conforms to the anatomy of the patient.

The wall of the tube 12 at the outer portion 14 is provided with a plurality of apertures defining the discharge openings 18. The discharge openings 18 are in spaced relation with the outer end 17 of the apparatus 11 so as to be located between the outer end and the plug 34 when the apparatus is in the esophageal mode. A sliding sleeve 37 surrounds the tube 12 in the area of the discharge openings 18 and upper and lower containing rings 38 and 39 define the limits of travel for the sleeve so that in one position, the openings are closed by the sleeve and in another position the openings are unrestricted by the sleeve.

In operation the inner portion 13 of the tube 12 is inserted orally or nasally into the patient's esophagus or trachea. During the insertion procedure, the inflatable cuff 21 is deflated and the lumen 15 of the tube 12 is open so that at no time during the insertion procedure is the patient's airway blocked. When the tube 12 is inserted in the trachea, the sleeve 37 is moved downwardly against the lower retaining ring 39 to seal the discharge openings 18 in the wall of the tube so that the flow of fluid is through the lumen 15. A conventional, open ended, cylindrical adapter, not shown, is inserted in the end of the tube for connection to a source of fluid. The inflatable cuff 21 is inflated to provide a seal with the walls of the trachea to prevent the passage of fluids between the external walls of the tube and the walls of the trachea and to aid in retaining the tube in place.

When utilized in the esophageal mode, the insertion of the tube 12 is as described above except that it is inserted in the esophagus rather than the trachea of the patient. Once inserted in the esophagus, the cuff 21 is inflated and the sleeve 37 is moved up against the upper retaining ring 38 so as to open the discharge openings 18. The adapter 16 is inserted in the upper end of the tube 12 so that the plug 34 is disposed beyond the openings 18 and fluids are introduced to the patient's lungs through the outer end 17, the outlet openings 18 and the trachea. The face mask 31, is preferably fitted snugly around the nose and mouth area of the patient's face, to prevent the escape of fluid through the nostrils or mouth during the inhalation step.

It is highly preferred that the apparatus 11 be utilized in conjunction with the face mask 31 when utilizing the apparatus in the esophageal mode. When so used, it is not necessary that the discharge openings 18 be disposed within the patient's mouth and throat region and excellent results are achieved when the discharge openings are located exteriorly of the tube 12 rather than in the walls of the tube.

As is more specifically shown in FIG. 3, a different embodiment of the adapter 16' is shown. The adapter 16' comprises a cylindrical portion 42 and a tapered portion 43 adapted to be inserted part way in the end of the tube 12. A plurality of slots 44 are provided around the periphery of the adapter wall and normally open exteriorly of the tube 12 to the interior of the face mask, not shown. A bottom wall 46 seals the bore of the adapter 16', 41 and cooperates with the walls of the tube 12 surrounding the tapered portion 43 of the adapter to seal the lumen 15 of the tube. Excellent fluid communication between the discharge slots 44 and the respiratory passage of the patient is achieved and the danger that all or a portion of the discharge slots will be blocked, as might be the case when the discharge openings are located in the patient's mouth and throat region, is avoided.

In the foregoing embodiments discussed in connection with FIGS. 2, 3 and 4, it is necessary to insert the adapter 16" after insertion of the inner portion 13 into the esophagus so as to avoid sealing the lumen 15 prior to initiation of the esophageal intubation procedure. Also, when utilizing the apparatus 11 of the present invention for endotracheal intubation, it is preferred practice to insert a conventional adapter in the tube, although the tube may be used alone without an adapter. In another embodiment of the present invention the adapter 16'" is modified for use both as an adapter for endotracheal intubation and for esophageal intubation eliminating the necessity of exchanging adapters.

As is more specifically shown in FIGS. 5, 6 and 7, the adapter 16" comprises an outer sleeve 47 having a cylindrical portion 48 and a tapered portion 49 adapted for part way insertion into the tube, not shown. A flange 51 is disposed adjacent the end of the outer sleeve 47 carried within the tube and extends normally inwardly to block a portion of the bore of the sleeve 47 to define an eccentrically disposed opening 52. A plurality of discharge slots 53 are disposed about the periphery of the outer sleeve 47.

The outer sleeve 47 may be formed integrally with the tube as it is not necessary that the adapter 16 be removable in this embodiment of the invention.

An inner sleeve 54, conforming substantially to the dimensions of the bore of the outer sleeve, is rotatably positioned within the outer sleeve and the bore of the inner sleeve defines the bore of the adapter 16". An O-ring or other suitable sealing means, not shown, may be disposed between the inner sleeve 54 and the bore of the outer sleeve 47 to provide a fluid tight seal therebetween. One end of the inner sleeve 54 terminates adjacent the flange 51 of the outer sleeve 47 and a portion 57 of the wall of the inner sleeve is inwardly biased to form a member blocking a portion of the bore of the inner sleeve and to define a restricted, eccentrically disposed opening 58 at the end of the inner sleeve adjacent the flange 51 of the outer sleeve 47. A bottom surface 60 is defined by the inwardly biased wall portion 57 and the bottom surface is contiguous with the upper surface of the flange 51 in one position and is disposed across the opening 52 when the inner sleeve 54 is rotated. The opposite end 58 of the inner sleeve 54 extends beyond the outer sleeve 47 to provide a gripping surface for rotating the inner sleeve and a point of connection of the adapter to a source of fluid.

A plurality of openings 59 are provided in the periphery of the inner sleeve 54. The openings 59 are longitudinally aligned with the discharge slots 53 and radially positioned for alignment to provide fluid communication through the discharge slots 53 and for misalignment to close the discharge slots 53 when the inner sleeve 54 is rotated.

The inner sleeve 54 is restrained from longitudinal movement within the outer sleeve 47 by a retainer ring 61 formed on the outer surface of the inner sleeve which is snap fitted into an annular recess 62 formed in the wall of the outer sleeve. Rotation of the inner sleeve 54 is limited by an inwardly extending pin 63 carried on the inner wall of the outer sleeve 47 which is received in a peripheral guide slot 64 formed on the outer wall surface of the inner sleeve so that rotation of the inner sleeve is permitted only between a first position and a second position.

As illustrated in FIGS. 5, 6 and 7, the adapter 16" is the endotracheal mode with the openings 52 and 58 aligned so that the bore of the adapter 16 is unsealed and the discharge slots 53 and openings 59 misaligned and thereby closed. By rotating the inner sleeve 54 until the pin 63 contacts the opposite edge of the slot 64, the adapter 16 is placed in the esophageal mode with the openings 52 and 58 misaligned and the bottom surface 60 of the inwardly sloped wall portion 57 of the inner sleeve 54 cooperating with the flange 51 of the outer sleeve 47 to seal the bore of the adapter 16. The discharge slots 53 of the outer sleeve 47 and the openings 56 of the inner sleeve 54 are radially aligned so as to permit fluid communication from the bore of the adapter to the respiratory passages of the patient in the manner previously described. Although not shown, a face mask is carried by the extending portion of the outer sleeve.

From the foregoing, it can be seen that the apparatus of the present invention is readily adapted to operate in endotracheal and esophageal intubation, depending on the circumstances of the patient and the skill and choice of the person performing the intubation. During the insertion procedure, the patient's airway is never closed, thereby avoiding the risk of asphyxiation during the insertion procedure, particularly where the operator is not highly skilled. When used in the esophageal mode, the reverse flow of fluids through the lumen of the tube is prevented by the seal carried by the adapter and the danger of aspiration of stomach fluids into the lungs is avoided. Prior to removal of the tube, stomach contents can be readily removed by insertion of a suction catheter through the tubular body into the stomach. The same apparatus is readily used for endotracheal intubation thereby eliminating the necessity of stocking more than one type of intubation apparatus.

The materials of construction of the apparatus of the present invention are those conventionally used for conventional esophageal and endotracheal intubators. The apparatus of the present invention can be constructed so as to be sterilizable and reusable or can be constructed so as to be disposable after a single use.

I claim:

1. An adapter for medical equipment designed for endotracheal and esophageal intubation, said adapter comprising:
    an outer sleeve having an open upper end and a lower end and a bore extending therebetween, a portion of said sleeve adjacent the lower end being adapted to be received in a tube for esophageal and endotracheal intubation, a wall member extending across the bore adjacent the lower end of said outer sleeve, said wall member having a first opening therein; the center of which is eccentrically disposed with respect to the longitudinal axis of the bore, and said outer sleeve further including a plurality of circumferentially arranged ports in the wall thereof located intermediate the upper end and the wall member;

an inner sleeve having an open upper and lower end, and a bore extending therebetween, said inner sleeve mounted within said outer sleeve and rotatable therein between a first and a second position with respect to said outer sleeve, the lower end of said inner sleeve being located adjacent the wall member of said outer sleeve, an inwardly extending member extending across a circumferential portion of the lower end of the bore of said inner sleeve defining a second opening at said lower end eccentrically disposed with respect to the longitudinal axis of said inner sleeve and in alignment with said first opening, whereby said inwardly extending member cooperates with the wall member of said outer sleeve to seal the bore of said inner sleeve when said inner sleeve is in the first position and the second opening of the inner sleeve is aligned with the first opening of said outer sleeve when said inner sleeve is in the second position, a plurality of circumferentially arranged ports opening through the wall of said inner sleeve, said ports being longitudinally aligned with the ports of said outer sleeve and registrable therewith when said inner sleeve is in the first position thereby to provide communication between the outside of said adapter and the bore of said inner sleeve and for being out of registration when said inner sleeve is rotated in the second position, whereby in the first position the ports of the said inner and outer sleeves are in registration for fluid communication from the bore to the exterior of said adapter and the bore of said inner sleeve is sealed and rotation of said inner sleeve to said second position simultaneously moves said ports out of registration thereby sealing the wall of said adapter and aligns the opening in the bore of the inner sleeve with the opening of the outer sleeve thereby providing fluid communication through the bore of said inner sleeve.

2. The adapter of claim 1 further including means for limiting the rotation of said inner sleeve in said outer sleeve between the first and second positions.

3. The adapter of claim 1 wherein a portion of the bore of said inner sleeve is biased inwardly in the direction of the lower end beginning at a point spaced away from the lower end thereby to define said inwardly extending member and to provide streamlined flow through said bore to the eccentrially disposed opening.

4. The adapter of claim 1 wherein the upper end of said inner sleeve extends longitudinally beyond the upper end of said outer sleeve.

* * * * *